United States Patent [19]

Nelson

[11] 4,045,871
[45] Sept. 6, 1977

[54] PALATAL EXPANDER
[75] Inventor: John E. Nelson, Holtwood, Pa.
[73] Assignee: HMW Industries, Inc., Lancaster, Pa.
[21] Appl. No.: 696,510
[22] Filed: June 16, 1976
[51] Int. Cl.² ............................................. A61C 7/00
[52] U.S. Cl. ..................................................... 32/14 E
[58] Field of Search ........................................ 32/14 E
[56] References Cited
U.S. PATENT DOCUMENTS

| 1,582,570 | 4/1926 | Brust | 32/14 E |
| 3,284,902 | 11/1966 | Dillberg et al. | 32/14 E |
| 3,977,082 | 8/1976 | Siztkowski | 32/14 E |

*Primary Examiner*—Robert Peshock
*Attorney, Agent, or Firm*—LeBlanc & Shur

[57] ABSTRACT

Disclosed is a device useful by an orthodontist for expanding a human palate. It comprises a stationary body secured to an anchor tooth on one side of the palate and a movable block secured to an anchor tooth on the other side of the palate. A helical spring urges the two apart to expand the palate. A keeper holds them together until they are fixed in place by the orthodontist.

16 Claims, 5 Drawing Figures

PALATAL EXPANDER

The present invention relates to an orthodontic appliance or device and more particularly to an intraoral orthodontic appliance having a coil spring for applying a force to anchor teeth in the human mouth.

In some instances such as where a person may have an unusually small mouth insufficient room exists in the mouth for a normal set of teeth. In situations of this type, certain teeth tend to become twisted or otherwise pushed out of place due to overcrowding spoiling a person's facial appearance and sometimes interferring with proper chewing.

Rather than pull certain teeth in order to avoid overcrowding, the orthodontist may wish to attempt to expand the palate to provide sufficient room. Other situations in which the orthodontist may wish to expand a palate is in certain limited situations where the upper and lower jaw structures are not identical in overall size and configuration. Since it is desirable to have the upper and lower teeth in at least substantial alignment, the orthodontist may wish to expand the palate to obtain this alignment.

Various devices have been proposed in the past for moving and/or aligning teeth in the human mouth. However, insofar as applicant is aware there is not presently available to the orthodontist a relatively simplified and inexpensive mechanical structure which may be inserted into the human mouth to expand the palate, which automatically effects palatal expansion. The present invention provides such a unit in the form of relatively movable and stationary members which may be normally retained in a close, side-by-side configuration by a removable keeper. One of the members is stationarily secured to one side of the palate while the other member telescopically received in and slidable with respect to the stationary member is secured to the other side of the palate. They are urged apart by a coil wound torsion spring. After the two members have been secured to anchor teeth on opposite sides of the plate, the keeper is removed and the mainspring freed to exert an expansion pressure on the palate of the wearer. As the expander gradually clefts the palate, cellular structure grows, filling the cleft as the maxilla is widened. Although the device is primarily constructed for use as a palatal expander and will be so described, it may also be used for palatal contraction by reversing the direction of the coil spring or torsion spring and changing the direction of the applied force.

It is therefore one object of the present invention to provide a simplified and relatively inexpensive palatal expander.

Another object of the present invention is to provide a device which may be used for either expanding or contracting the palate in a human mouth.

Another object of the present invention is to provide a palatal expander which may be simply inserted and applied to anchor teeth in the mouth by an orthodontist.

Another object of the present invention is to provide a palatal expander which applies a substantially constant force to anchor teeth on opposite sides of a human palate.

Another object of the present invention is to provide a palatal expander in which telescoping elements are forced apart by torsion force of a conventional mechanical wristwatch mainspring.

These and further objects and advantages of the invention will be more apparent upon reference to the following specification, claims and appended drawings wherein:

Figure 1:
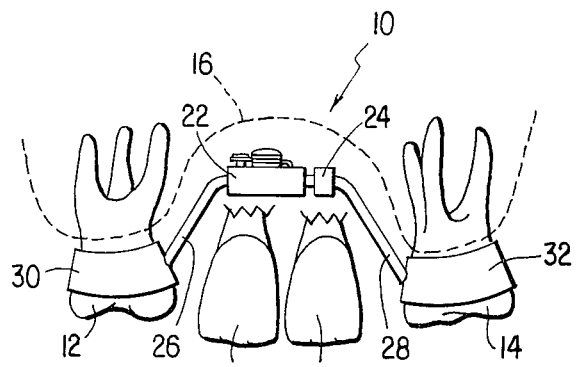
FIG. 1 is a diagrammatic view of a portion of a human palate and teeth showing the palate expander of the present invention as initially inserted in the mouth.
Figure 2:
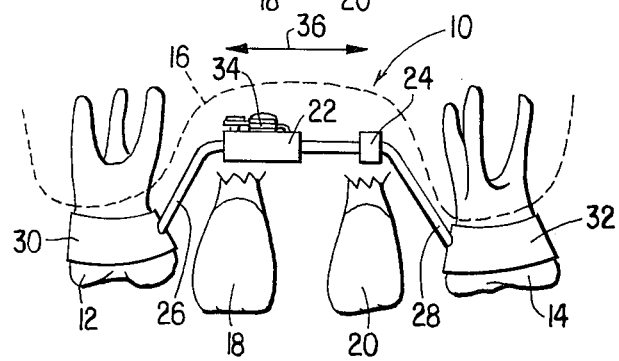
FIG. 2 is a view similar to FIG. 1 showing the expander after it has clefted the palate.

Referring to the drawings, the palate expander of the present invention is generally illustrated at 10 in FIG. 1. It is illustrated as applied to two pair of anchor teeth (two each side) such as 12 and 14 in the form of human molars extending downwardly from a human palate generally outlined by the dashed line 16. A pair of central incisors extending from the same palate are shown at 18 and 20. The expander is shown in FIGS. 1 and 2 as generally comprising a stationary body 22 and movable block 24 attached to respective metal legs 26 and 28. These are in turn connected to the respective bands 30 and 32 surrounding the molars 12 and 14.

FIG. 2 shows the block 24 as having moved away from the body 22. This is done under the urging of a coil spring generally indicated at 34 preferably in the form of a conventional mechanical wristwatch mainspring. As illustrated in FIG. 2, both the anchor teeth 12 and 14 and the central incisors 18 and 20 have separated relative to the position illustrated in FIG. 1 indicating in FIG. 2 that the expander has clefted the palate. It is understood that in treatment of this type cellular structure grows, filling the cleft as the maxilla is widened. The separating force exerted by the spring 34 in FIG. 2 is illustrated by the double ended arrow 36.

Figure 3:
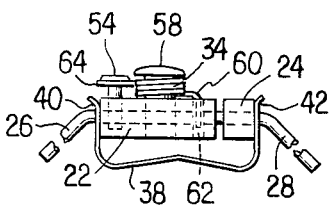
FIG. 3 is a view of the palate expander by itself with the keeper in place.

FIG. 3 is a view of the palatal expander 10 in the closed or unexpanded position and retained by a substantially U-shaped keeper 38 having ends 40 and 42 which engage and retain the body 22 and movable block 24. The expander is inserted into the mouth in the position illustrated in FIG. 3 and the legs attached to the anchor teeth. When the device has been completely attached, and only then, the keeper 38 is removed so that the force of the spring 34 is exerted on the block 24.

Figure 4:
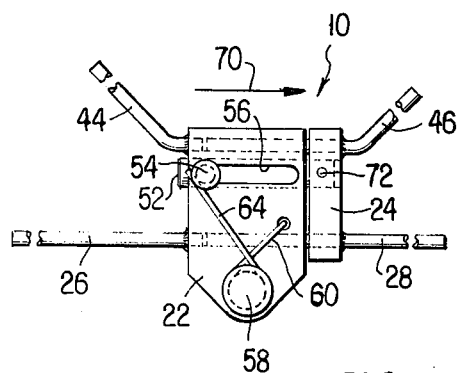
FIG. 4 is a plan view of the palatal expander with the movable elements in the retracted or compressed position.
Figure 5:
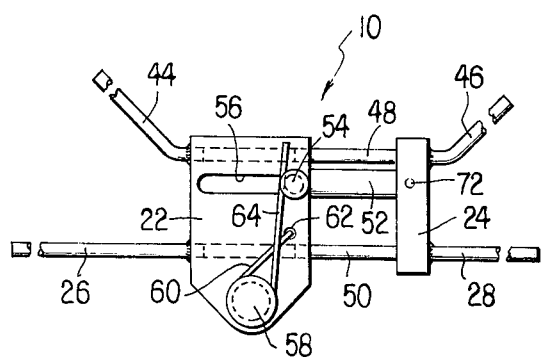
FIG. 5 is a plan view similar to FIG. 4 with the movable elements in the open or expanded position.

FIG. 4 is a plan view of the expander 10 in the collapsed position with the keeper removed and FIG. 5 is a similar plan view of the device in the expanded position. In addition to the front legs 26 and 28 previously described block 22 is connected to a downwardly and rearwardly extending back leg 44 and block 24 is connected to a similar back leg 46. These are normally connected to the backside of the bands 30 and 32 on the same molars 12 and 14 as the front legs 26 and 28. Attached to movable block 24 and slidably received in suitable apertures in the body 22 are a pair of spaced guide legs 48 and 50 and a force receiver 52. The force receiver carries a push pin 54 slidable in a slot 56 in the body 22.

Spring 34 is of helical coil construction and is wrapped around a post 58. One end of the spring as indicated at 60 is turned over and received in a hole 62 in the body 22. The other end of the spring as indicated at 64 bears against push pin 54. When the keeper 38 is removed, coil spring 34 urges the two members to separate from the position illustrated in FIG. 4 to the completely expanded position illustrated in FIG. 5. Spring 34 acts as a torsion spring and exerts a force approximately in the direction illustrated by the arrow 70 in FIG. 4. Outward movement of block 24 is limited by engagement of the push pin 54 with the other end of slot 56 in body 22. Force receiver 52 carrying push pin 54 is secured to block 24 in a suitable manner such as by a pin 72 passing through the block and receiver. Guide legs 48 and 50 are similarly secured to the movable block in a desired manner such as by soldering, braising or the like. All of the elements illustrated are preferably of metallic construction for strength since the device is of relatively small size so that it may be inserted into and removed from a human mouth.

It is apparent from the above that the present invention provides a simplified and relatively inexpensive palatal expander and in particular one which may be simply applied to and removed from a human mouth. The expander is inserted with the keeper 38 so that attachment to the teeth is easy for the orthodontist. Removal is facilitated in a like manner by simply removing the bands 30 and 32 from the molars 12 and 14.

Although the device is primarily designed as a palatal expander and has been so described, it is understood that it may also be used for palatal contraction. This can be simply accomplished by reversing the direction of force of the torsion spring 34 and moving the long arm 64 of the spring to the other side of pin 54. In this case, suitable removable plus may be inserted in the space between the body and block to keep it in the expanded position illustrated in FIG. 5 until it has been attached to the teeth and then the separating block removed by the orthodontist in the same manner that the keeper 38 is removed when the device is formed as an expander.

The invention may be embodied in other specific forms without departing from the spirit or essential characteristics thereof. The present embodiment is, therefore, to be considered in all respects as illustrative and not restrictive, the scope of the invention being indicated by the appended claims rather than by the foregoing description, and all changes which come within the meaning and range of equivalency of the claims are, therefore, intended to be embraced therein.

What is claimed and desired to be secured by United States Letters Patent is:

1. An orthodontic device for intraoral use comprising a body, means carried by said body for connecting said body to an anchor tooth on one side of a human palate, a block joined to said body or relative movement between the two, means carried by said block for connecting said block to an anchor tooth on the other side of a human palate, a bias spring acting between said body and block for producing relative movement between them, and removable means engaging both said body and said block for preventing said relative movement until said device has been installed in a human mouth.

2. A device according to claim 1 wherein said bias spring is anchored to said body and acts against said block.

3. A device according to claim 2 wherein said block carries a pin, said spring bearing against said pin.

4. A device according to claim 3 wherein said body carries a post, said spring being wrapped around said post.

5. A device according to claim 4 wherein said means carried by said body and block for connecting them to anchor teeth comprise a pair of legs extending outwardly from each.

6. An orthodontic device for intraoral use comprising a body, means carried by said body for connecting said body to an anchor tooth on one side of a human palate, a block joined to said body for relative movement between the two, means carried by said block for connecting said block to an anchor tooth on the other side of a human palate, a bias spring acting between said body and block for producing relative movement between them, and removable means engaging both said body and said block for preventing said relative movement until said device has been installed in a human mouth, said bias spring being anchored to said body and acting against said block, said block carrying a pin, said spring bearing against said pin, said body carrying a post, said spring being wrapped around said post, said body including a pair of apertures, said block having a pair of guides slidable in said apertures.

7. An orthodontic device for intraoral use comprising a body, means carried by said body for connecting said body to an anchor tooth on one side of a human palate, a block joined to said body for relative movement between the two, means carried by said block for connecting said block to an anchor tooth on the other side of a human palate, a bias spring acting between said body and block for producing relative movement between them, and removable means engaging both said body and said block for preventing said relative movement until said device has been installed in a human mouth, said bias spring being anchored to said body and acting against said block, said block carrying a pin, said spring bearing against said pin, said body carrying a post, said spring being wrapped around said post, said block including a force receiver slidably coupled to said body, said pin being mounted on said force receiver.

8. An orthodontic device for intraoral use comprising a body, means carried by said body for connecting said body to an anchor tooth on one side of a human palate, a block joined to said body for relative movement between the two, means carried by said block for connecting said block to an anchor tooth on the other side of a human palate, a bias spring acting between said body and block for producing relative movement between them, and removable means engaging both said body and said block for preventing said relative movement until said device has been installed in a human mouth, said bias spring being anchored to said body and acting against said block, said block carrying a pin, said spring bearing against said pin, said body carrying a post, said spring being wrapped around said post, said means carried by said body and said block for connecting them to anchor teeth comprising at least one leg extending outwardly from each.

9. A device according to claim 8 wherein said legs are each secured to a metal band adapted to surround an anchor tooth.

10. A palatal expander comprising a body, an outwardly extending leg carried by said body, a band for surrounding a molar on one side of a human palate connected to said leg, a block slidably joined to said body, an outwardly extending leg carried by said block, a second band for surrounding a molar on the other side of a human palate connected to the leg on said block, a spring attached to said body and bearing against said block to urge said body and block apart, and a keeper removably secured to said body and block for holding said body and block together until said expander is secured in a human mouth.

11. An expander according to claim 10 wherein said keeper engages the outer edges of said body and block to hold them together.

12. An expander according to claim 11 wherein said keeper is substantially U-shaped with its legs slidably received over the outer edges of said body and block.

13. An expander according to claim 10 wherein said block is slidably joined to said body by a force receiver, said spring bearing on said block force receiver.

14. An expander according to claim 13 wherein said body includes a post, said spring being wrapped around said post.

15. An expander according to claim 14 wherein said force receiver includes a pin, said spring having an end bearing on said pin.

16. An expander according to claim 15 wherein said block includes a pair of guides slidably received in said body.

* * * * *